United States Patent [19]

Heyer

[11] Patent Number: 4,534,762

[45] Date of Patent: Aug. 13, 1985

[54] VASCULAR PUNCTURE DRESSING

[76] Inventor: Hal B. Heyer, 5546 Perry Ave. N., Crystal, Minn. 55429

[21] Appl. No.: 453,606

[22] Filed: Dec. 27, 1982

[51] Int. Cl.³ ............................................. A61M 25/02
[52] U.S. Cl. ............................. 604/180; 128/DIG. 26
[58] Field of Search ........................ 604/180, 179, 174; 128/DIG. 26, 133, 132

[56] References Cited

U.S. PATENT DOCUMENTS

| | | | |
|---|---|---|---|
| 2,821,194 | 1/1958 | Simmons | 604/180 |
| 3,782,378 | 1/1974 | Page | 128/133 |
| 3,927,676 | 12/1975 | Schultz | 128/DIG. 26 X |
| 4,057,066 | 11/1977 | Taylor | 128/DIG. 26 X |
| 4,122,857 | 10/1978 | Haerr | 604/180 |
| 4,221,215 | 9/1980 | Mandlebaum | 128/DIG. 26 X |

Primary Examiner—Stephen C. Pellegrino
Attorney, Agent, or Firm—Hugh D. Jaeger

[57] ABSTRACT

A vascular puncture dressing is described. The dressing includes a pressure-sensitive adhesive tape section, and at least a pair of adhesive strips extend forwardly from the forward edge of the dressing. The dressing preferably is transparent at least in an area adjacent the forward edge so that the vascular puncture wound can be observed without removal of the dressing.

3 Claims, 5 Drawing Figures

VASCULAR PUNCTURE DRESSING

FIELD OF THE INVENTION

The invention relates generally to the field of medicine, and particularly to dressings useful in vascular puncture procedures to reduce the likelihood of trauma and infection.

BACKGROUND OF THE INVENTION

Many millions of venipuncture procedures are performed each year in hospitals in the United States. In such procedures, a cannula, which may be a steel needle or a plastic tube, is inserted in a vein with the exterior end of the cannula being fitted with a hub adapted for connection to a tube through which fluids of various types are to be intravascularly administered. In the most common venipuncture procedure, a cannula, usually either a hollow steel needle or a plastic tube within which is carried a rigid, removable sharpened stylet, is passed through the skin and into the lumen of a vein. Tubing is then attached to the hub of the cannula, and is commonly taped to the patient's skin. To anchor the cannula in place, strips torn from a roll of adhesive tape commonly are wound about the hub of the cannula and the ends of each strip are adhered to the patient's skin on either side of the venipuncture site to restrain back and forth movements of the hub and cannula. One or more further strips of protective adhesive tape are then adhered to the skin over the venipuncture site to further stabilize the cannula. The vascular puncture site itself may be treated with an antiseptic to reduce infection.

The taping of the hub of the cannula in place against the skin, as described above, is time consuming, requires considerable harmful manipulation of the cannula and hub, and completely shields from view not only the venipuncture site but also the cannula hub itself. Cannula hubs are commonly of plastic and are generally color coded to signal the diameter of the cannula. For certain procedures, it is necessary that the cannula diameter be able to be determined without the necessity of withdrawing the cannula from the vein and inserting a separate cannula.

Unfortunately, vascular puncture wounds often become infected, and postinfusion phlebitis may occur. The completed cannula site may be correctly considered to be an open surgical wound containing a foreign body. Bacteremia, the most serious infection complication related to infusion therapy, reportedly may occur in up to eight percent of patients with plastic catheters or cannulae in place. Contaminants leading to infection may be carried by the infusion devices, or may merely enter directly through vascular puncture wounds. In the latter situation, it appears that the likelihood of infection increases as the catheter is inadvertently manipulated during application of the catheter dressing or as the dressing is changed.

It is commonplace for health professionals to prepare for a vascular puncture procedure by tearing strips of tape from a roll, temporarily fastening the strips of tape to a convenient surface such as the edge of an operating room table, introducing the cannula into a vein, and then plucking the strips one by one from the side of the table to anchor the cannula hub in place. Such procedures, even when conducted in operating room conditions, are far from sterile.

As thus described, vascular puncture procedures in the past have involved the use of tape strips torn from a roll of tape by health professionals performing the procedures. The resulting dressings accordingly are not uniform, are not sterile, require an inordinate amount of time to prepare, require significant manipulation of the catheter and hub during application and changing of the dressing, and tend to shield both the vascular puncture wounds and the cannula hubs from view. Reference may be made to Arnold, et al, *The Importance of Frequent Examination of Infusion Sites in Preventing Postinfusion Phlebitis, Surgery, Gynecology and Obstetrics,* 145: 19–20 (1977); Stratton, *Infection Related to Intravenous Infusion,* Heart and Lung, Vol. II, No. 2, 1982, pp. 123–137; Maki, *The Prevention and Management of Device-Related Infection in Infusion Therapy,* Journal of Medicine, Vol. II, No. 4, 1980; and McIntyre et al, eds., *Textbook of Advanced Cardiac Life Support,* pub. by the American Heart Association, 1981, Chap. II.

BRIEF DESCRIPTION OF THE INVENTION

The invention provides a new and useful, vascular puncture dressing that greatly reduces the amount of time required to apply the dressing to a vascular puncture wound and that renders the wound site and the cannula hub visible to an observer.

The dressing in one embodiment comprises means defining a section of flexible adhesive tape having forward and rearward edges, and means defining at least a pair of adhesive tape strips carried by the dressing and extending forwardly of the forward edge of the adhesive tape section, the strips being adapted to be wrapped about the hub of a cannula that extends into a vascular puncture wound and adhered to a patient's skin adjacent the wound or to the body of the dressing to stabilize the hub against movement. Desirably, at least one portion of the section is transparent to permit viewing of the wound site. The adhesive tape materials employed in the invention are flexible and conformable, and comprise a flexible backing and a layer of pressure-sensitive adhesive carried by the backing. The dressings desirably include readily removable liners carried by and protecting the adhesive layers. The liners may readily be removed from the dressing to expose the adhesive layers when the dressing is to be applied to a vascular puncture.

DESCRIPTION OF THE PREFERRED EMBODIMENT

Figure 2:
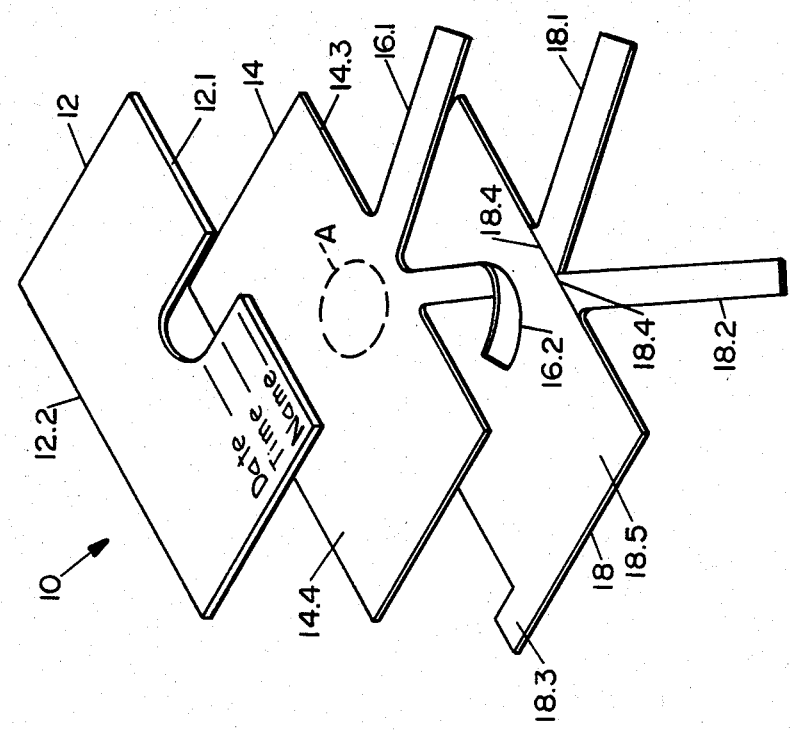
FIG. 2 is an exploded, perspective view of one embodiment of a device of the invention.
Figure 1:
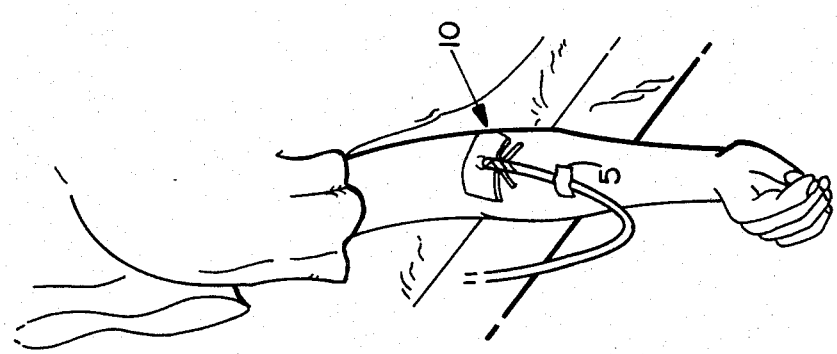
FIG. 1 is a partial, diagramatic view of a device of the invention applied to a patient's arm.
Figure 5:
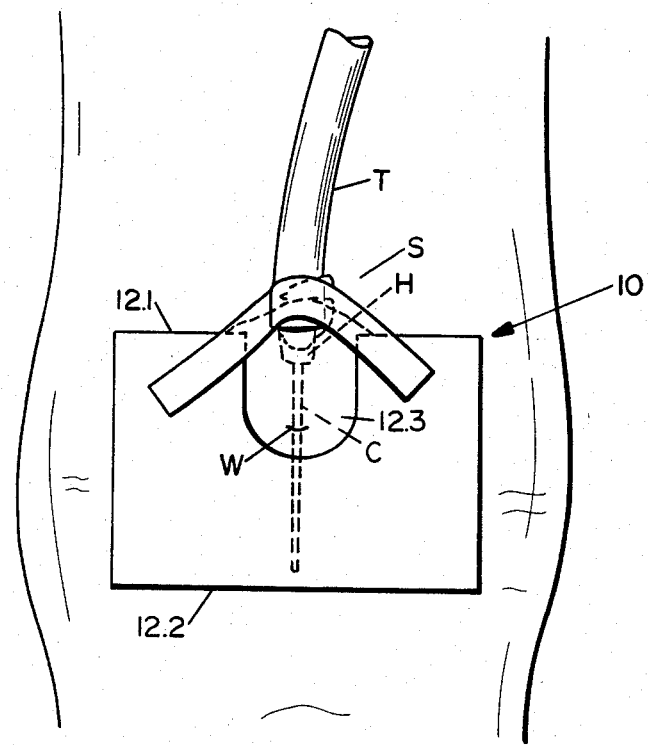
FIG. 5 is a diagramatic view of a device of the invention as the same may be applied to a patient.

An embodiment of the invention is depicted as (10) in FIGS. 1, 2 and 5, and includes a flexible, conformable section of pressure-sensitive adhesive tape (12) having forward and rearward edges (12.1, 12.2). The section (12) is provided with a forwardly facing recess (12.3) that may be generally semicircular as shown in FIGS. 2 and 5 or may be rectangular or any other suitable shape.

The adhesive tape section (12) is sufficiently flexible and conformable as to conform closely to the skin of a patient, and generally consists of a layer of backing material (12.4) on one side of which is carried a pressure-sensitive adhesive layer (12.5). Its reverse or outer surface may carry indicia for identification of the health professional and the date and time the dressing was applied.

Figure 3:
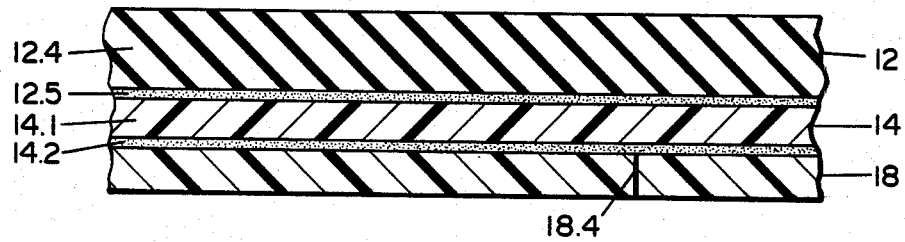
FIG. 3 is a broken-away, cross-sectional view of the assembled device of FIG. 2.
Figure 4:
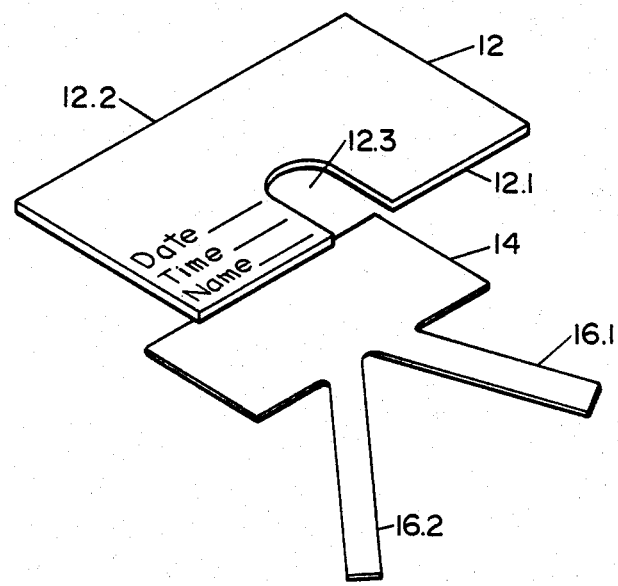
FIG. 4 is an exploded, perspective view similar to that of FIG. 2 but showing another embodiment of the invention.

Adhered to the pressure-sensitive adhesive surface (12.5) is a transparent sheet (14) which, in the embodiments shown in the drawing, may be a section of transparent adhesive tape having a backing layer (14.1) and an adhesive layer (14.2). The adhesive tape section (14) may be the same size as the section (12), as shown in FIG. 2, or may be somewhat smaller than the section (12) as shown in FIG. 4, but is large enough to cover the recess (12.3). Shown as extending forwardly of the transparent adhesive tape section (14) are at least one pair of flexible, conformable adhesive tape strips designated (16.1, 16.2) such that when the layers (12) and (14) are assembled as shown in FIG. 3, the strips (16.1, 16.2) extend forwardly of the forward edge (12.1) of the adhesive tape section (12). Although three or four or more such strips may be used, a single pair of strips is preferred.

Shown at (18) in FIGS. 2 and 3 is a liner, which in a preferred embodiment may consist of a sheet of paper coated with a release substance such as a silicone to permit it to be easily stripped from the adhesive layer (14.2) in a known manner. The liner (18) may include forwardly extending strips (18.1, 18.2) that are preferably separate and that are adhered to the respective transparent adhesive tape strips (16.1, 16.2). The purpose of the liner (18) is to protect the adhesive layer (14.2), the liner being easily removable to expose the adhesive layer (14.2) so that the latter may be applied to the skin of a patient. The liner (18) may include an outwardly projecting tab, typified at (18.3), to facilitate its easy removal from the dressing. The liner (18) may be slit, as shown at (18.4), so that the liner portions (18.1), (18.2) underlying the strips (16.1), (16.2) may be removed separately from the body (18.5) of the liner underlying the body (14.4) of the adhesive tape section (14.).

The adhesive tape section (12) desirably is provided with a limp backing (12.4) of a suitable fabric, woven or nonwoven, or of plastic such as the various foamed plastics including polyurethane foams or the like, of the types currently in commercial use. The adhesive layer (12.5) may be hypoallergenic. The adhesive tape section (14) may be substantially any of the transparent pressure-sensitive adhesive tapes in current commercial usage. The adhesive layer (14.2), similarly, may be hypoallergenic. The liner (18) may be of kraft paper or the like suitably coated with a release agent from which the adhesive layer (14.2) can be easily stripped.

Referring now to the embodiment of FIG. 4, the transparent adhesive tape section (14), as noted above, may be somewhat smaller in dimension than the overlying tape section (12), and the adhesive layer (12.5) of the latter tape section may be brought into contact with the skin of a patient to hold the dressing in place. In the embodiment of FIG. 4, the adhesive side of the transparent tape section (14) may, if desired, face toward and contact the overlying tape section (12), in which event one liner, similar to that shown as (18) in FIG. 2, may be placed in protective contact with the adhesive layer (12.5) of the tape section (12) and other strips of liner may be placed over and in protective contact with the adhesive layer carried by the strips (16.1, 16.2). In the embodiment shown in the drawing, the transparent tape section (14) extends across and, with the recessed portion (12.3) of the adhesive tape section (12), defines a window through which a vascular puncture wound can be viewed to see if skin redness or swelling indicative of infection develops about the wound site. It will now be understood that the transparent tape section (14) also serves structurally to support the portions of the adhesive tape section (12) on either side of the recess (12.3).

In one embodiment, the invention relates to a dressing having a pressure-sensitive adhesive tape section such as that shown at (14) in FIG. 2, the tape section including adhesive tape strips (16.1, 16.2) extending from its forward edge (14.3). The adhesive tape section (14) in this embodiment desirably is transparent, thereby affording a clear and unhindered view of the venipuncture site. A liner, such as that shown at (18) in FIG. 2, is desirably employed to protect the adhesive layer of the tape section (14) prior to use. The transparent tape section (14) desirably is not only flexible, but also has some ability to stretch under tensile stresses so as to conform closely to the surface anatomy of a patient.

In another embodiment, the strips (16.1, 16.2), may simply be attached to the underside of the overlying adhesive tape section (12), the adhesive tape sections criss-crossing and hence covering the recess (12.3). The most preferred embodiment comprises a single section of flexible, conformable, transparent, pressure-sensitive adhesive tape as shown at (14) in FIG. 2 and having a body portion (14.4) from a forward edge (14.3) of which forwardly extends a pair of strip portions (16.1), (16.2). Underlying the body and strip portions are separately removable release liner portions (18.1), (18.2) and (18.5).

In use, the dressing of the invention commonly will be supplied in a sterilized package that is to be opened immediately before use. If desired, a suitable antiseptic may be incorporated into the dressing immediately beneath that portion of the dressing overlying the venipuncture wound, such antiseptic being typified by "A" in FIG. 2 of the drawing. With reference to FIG. 5, after disinfecting the skin "S", a cannula is inserted through the skin and into the lumen of a vein, the cannula being designated "C" in FIG. 5 and the vascular puncture wound being designated as "W". The cannula terminates outwardly in a hub "H" which commonly is color-coded to designate the diameter of the cannula. When the cannula has been appropriately positioned within a vein, suitable tubing, which may carry pinch clamps, access ports or other accessories known to the art, is attached to the hub, the tubing being designated "T" in FIG. 5. The cannula and hub thus extend at a slight angle to the skin surface surrounding the wound site "W", and the tubing desirably is held in place by means of a small adhesive strip "S" in FIG. 1 attached to the skin of the patient, all in a manner common to the art.

The dressing (10) is removed from its sterile packaging, the body (18.5) of the release liner (18) is removed and discarded, and the dressing is then placed over the puncture wound in the manner shown in FIG. 5, the wound being visible to an observer as described above. Upon removal of the liner portions (18.1), (18.2), the adhesive tape strips (16.1, 16.2), which desirably extend in a generally "V" orientation forwardly of the forward edge (12.1) of the dressing, are then wrapped about the hub and are applied to the skin of the patient on either side of the hub (FIG. 2) or are brought rearwardly and adhered to the outer surface of the dressing, as shown in FIG. 5. The strips (16.1, 16.2) preferably completely encircle the hub (H). In this manner, the hub is prevented from back and forth movements, thereby reducing trauma to the wound "W" and avoiding movement of the cannula "C" within the lumen of the vein. Both the wound site and the hub are thus visible to the observer.

In practice, a standard dressing of the prior art, which was prepared by tearing strips from a roll of adhesive tape in the manner referred to above, was compared to a dressing of the invention similar to that of FIG. 2 but having transparent adhesive strips (16.1, 16.2) extending in a criss-cross fashion beneath the recess (12.3) in the adhesive tape section (12), the section (12) and the strips (16.1) and (16.2) each bearing separate liners. An anesthesiologist, skilled in vascular puncture procedures for administering anesthetics and other medicines to patients during surgical operations, compared the speed and ease with which the prior art dressings and dressings of the invention could be applied to patients. It was found that whereas the prior art dressing took minutes to prepare and apply, and resulted in some undesirable manipulation of the hub and cannula, the dressing of the invention could be applied in much less than one minute and resulted in a reduction in the manipulation of the cannula and hub and further provided the anesthesiologist, and subsequent health professionals, with a clear view of the puncture site and of the hub color. The puncture site thus could be directly observed for signs of infection without removal of the dressing, thereby avoiding the necessity of removing the dressing for examination of the wound with the attendant trauma induced by movement of the cannula and hub. Knowledge of the hub color, and hence of the cannula diameter, is necessary in the event that immediate infusions of blood or blood products or drugs is required in emergency situations.

While a preferred embodiment of the present invention has been described, it should be understood that various changes, adaptations and modifications may be made therein without departing from the spirit of the invention and the scope of the appended claims.

What is claimed is:

1. A dressing for covering a vascular puncture wound and for stabilizing a cannula extending into the wound against movement, the dressing comprising means defining a section of adhesive tape having forward and rearward edges and having a recess in said forward edge through which a vascular puncture wound may be observed; means defining a transparent sheet carried by the section of adhesive tape and extending across said recess, and means defining at least a pair of flexible tape strips carried by the dressing and extending forwardly beyond the forward edge of the adhesive tape section and adapted to be wrapped about the hub of a cannula and adhered to a patient's skin adjacent a puncture wound or to the dressing to stabilize the hub against movement.

2. The dressing of claim 1 wherein the pair of adhesive tape strips are transparent to permit observation of a cannula hub about which the strips are to be wrapped.

3. The dressing of claim 1 wherein the adhesive tape section and adhesive tape strips respectively comprise a flexible backing and a pressure-sensitive adhesive layer carried by the backing, and further including releasable liner means carried by and protecting said adhesive layers and readily removable therefrom to expose said adhesive layers when the dressing is to be applied to a vascular puncture wound.

* * * * *